United States Patent [19]

Haber et al.

[11] Patent Number: 4,826,484
[45] Date of Patent: May 2, 1989

[54] DISEASE CONTROL SYRINGE HAVING A RETRACTABLE NEEDLE

[75] Inventors: Terry M. Haber, Lake Forest; William H. Smedley, Lake Elsinore; Clark B. Foster, El Toro, all of Calif.

[73] Assignee: Habley Medical Technology Corporation, Laguna Hills, Calif.

[21] Appl. No.: 25,419

[22] Filed: Mar. 13, 1987

[51] Int. Cl.$^4$ ............................................. A61M 5/00
[52] U.S. Cl. ................................... 604/110; 604/195; 604/228
[58] Field of Search ............... 604/110, 111, 196, 197, 604/218, 187, 195, 228

[56] References Cited

U.S. PATENT DOCUMENTS

| | | | |
|---|---|---|---|
| 3,320,954 | 5/1967 | Cowley | 604/110 |
| 4,026,287 | 5/1977 | Haller | 604/195 |
| 4,507,117 | 3/1985 | Vining et al. | 604/196 |
| 4,562,844 | 1/1986 | Carpenter et al. | 604/228 |
| 4,643,199 | 2/1987 | Jennings, Jr. et al. | 604/110 |
| 4,650,468 | 3/1987 | Jennings, Jr. | 604/110 |
| 4,692,156 | 9/1987 | Haller | 604/195 |

Primary Examiner—John D. Yasko
Attorney, Agent, or Firm—Morland C. Fischer

[57] ABSTRACT

A disposable disease control syringe which reduces the frequency of accidental needle strikes to health care workers and prevents health-threatening reuse of the needle cannula by drug abusers. The syringe includes a cylinder having an open proximal end, a closed distal end, and a needle projecting through the distal end. A piston assembly having a detachable stem and a needle capturing receptacle moves axially through the syringe cylinder to expulse fluid medication and to selectively engage the needle at the most distal aspect of the cylinder. The stem is then withdrawn from the cylinder through the open proximal end thereof, whereby to relocate the needle from the distal to the proximal cylinder end. The needle capturing receptacle is locked at the proximal end of the syringe cylinder, such that the needle cannula extends from the proximal end and is completely shielded by the cylinder. The stem is then detached from the piston assembly and discarded, thereby leaving a disposal cartridge with the needle cannula rendered permanently irretrievable therewith.

12 Claims, 3 Drawing Sheets

DISEASE CONTROL SYRINGE HAVING A RETRACTABLE NEEDLE

BACKGROUND OF THE INVENTION

1. FIELD OF THE INVENTION

This invention relates to a disposable disease control syringe which is adapted to reduce the frequency of accidental and, in some cases, life threatening needle strikes while reducing instances of possible drug abuse and the spread of contagious disease by preventing reuse of the syringe by drug abusers.

2. PRIOR ART

Hypodermic syringes are used for a variety of injection procedures including the delivery of medicinal drugs to a recipient. However, once the injection procedure is completed and the syringe cylinder emptied, problems may arise as a consequence of failing to properly and adequately dispose of the syringe. By way of a first example, the syringe may be used to treat a patient having a communicable disease. To prevent reuse, the hypodermic needle is sometimes broker before the syringe is discarded. Health care workers are susceptible to accidental and potentially infectious needle strikes due to the careless handling of the hypodermic needle when breaking the needle or disposing of the syringe after use. The resulting mini-accidents caused by an accidental needle strike typically require a blood test for such disease as AIDS and hepatitis. The corresponding cost and inefficiency of testing health care workers who have received an inadvertent needle strike result in considerable waste, which may be particularly damaging to a health care facility striving for economy and efficiency. By way of a second example, drug users have been known to rummage through the trash of a health facility in an effort to find emptied syringes which have been discarded after use. Such syringes are often reused in an illicit capacity, whereby to promote drug abuse and the possible spread of contagious disease.

The following U.S. Patents provide examples of syringes having a hypodermic needle which may be withdrawn into the syringe cylinder after use:

U.S. Pat. No. 2,722,215; Nov. 1, 1955
U.S. Pat. No. 4,026,287; May 31, 1977
U.S. Pat. No. 4,507,117; Mar. 26, 1985

The aforementioned patents provide no way by which to render the needle permanently irretrievable within and shielded by the cylinder, so that the syringe and needle are not reusable. That is to say, nothing is provided to prevent the needle from being completely removed from the syringe cylinder and/or from being returned to an outwardly projecting position from the cylinder by which to execute another injection procedure. Consequently, the syringe may be reused. Moreover, a greater opportunity exists to handle a needle which has been removed from or returned to the cylinder, so as to disadvantageously contribute to accidental needle strikes and the possible spread of disease.

SUMMARY OF THE INVENTION

In general terms, a disposable disease control syringe is disclosed which overcomes the problems inherent in a conventional syringe by reliably reducing the frequency of accidental needle strikes among health care workers while preventing reuse of the needle by drug users. The syringe includes a cylinder or barrel having a closed distal end and an open proximal end. A first end of a needle projects outwardly from the distal cylinder end, by which a fluid may be injected or infused in the conventional manner. A second end of the needle extends into the interior of the cylinder and terminates at a relatively large needle catch.

The syringe also includes a piston which is adapted for reciprocal and axial movement through the syringe cylinder. The piston comprises the detachable connection of an elongated piston stem to a sealing and locking assembly. An elastomeric seal, formed at one end of the sealing and locking assembly, functions as a plunger head when the piston is moved axially through the syringe cylinder during a fluid injection procedure. The seal is mounted around a plurality of flexible legs which define a needle capturing receptacle therebetween. When the piston is moved through the syringe cylinder at the conclusion of a fluid injection procedure, the elastomeric seal is compressed against the most distal aspect of the cylinder, such that the needle capturing receptacle is advanced axially into engagement with the needle catch. The needle catch is thereby snapped into receipt by the receptacle.

The piston stem is now withdrawn through the open proximal end of the syringe cylinder, whereby to relocate the needle from the distal end to the proximal cylinder end, such that the needle cannula extends through the interior of the syringe cylinder from the proximal end thereof. At the same time, the sealing and locking assembly is permanently locked across the proximal end of the cylinder to both block the removal of the needle from the cylinder and prevent any return of the needle from the proximal end to the distal cylinder end. The piston stem is then detached from the piston by breaking the stem away from the sealing and locking assembly.

The syringe may then be discarded in a normal fashion. However, by virtue of the present invention, the resulting cartridge is rendered safe by locking the needle within the syringe cylinder, so that the needle is completely shielded by and rendered totally irretrievable therewithin. Accordingly, the syringe cannot be reused. Moreover, the used syringe is in a condition to permit safe disposal without requiring handling or cutting of the needle as has heretofore been necessitated as a consequence of many conventional syringe assemblies.

DESCRIPTION OF THE PREFERRED EMBODIMENT

Figure 1:
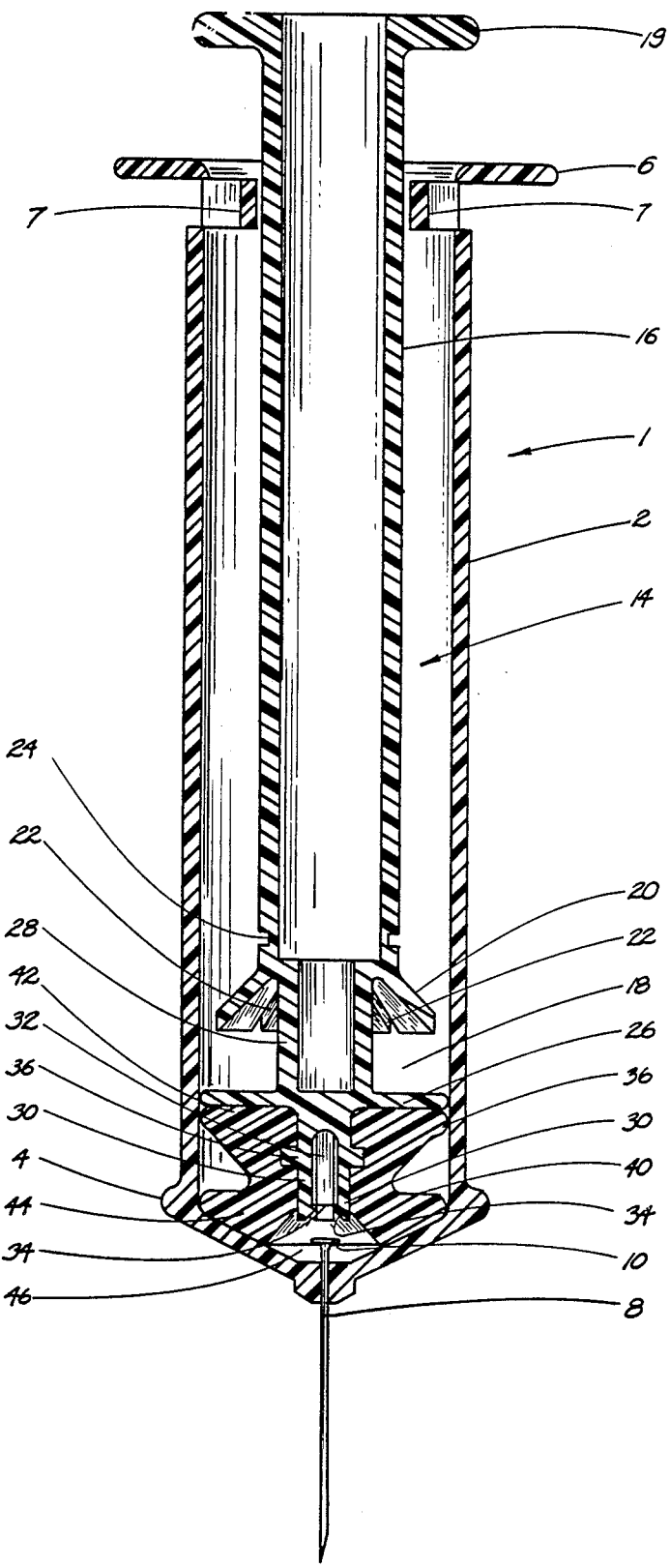
FIG. 1 is a cross-section of the syringe which forms the present invention showing a piston moved to a distal end of the syringe cylinder.

The disease control syringe having a retractable needle which forms the present invention is best described while referring to the drawings. In FIG. 1, there is shown the syringe 1 including a generally cylindrical cylinder or barrel 2 having an open proximal end and a closed distal end. An anti-slip flange 4 is disposed around the distal end and a major flange 6 is disposed around the proximal end of the cylinder 2. The use of the flanges 4 and 6 will soon be described. A pair of internal locking tabs 7 are formed at the proximal end of cylinder 2 below the major flange 6 thereof. In the embodiment shown in FIG. 1, the locking tabs of syringe 1 are formed by compressing opposite sides of the cylinder 2 to form an area of reduced diameter adjacent the opening at the proximal end thereof. However, it is to be understood that the locking tabs may be formed by any suitable means to establish an area of reduced diameter at the proximal cylinder end. An opening is formed in the closed distal end of syringe cylinder 2. The opening is sized to receive the cannula of a hollow needle 8 therethrough during the manufacture of the syringe 1. The needle cannula is retained in a tight fit within the distal hole of cylinder 2. Needle 8 has a sharp cutting surface formed at a distal end thereof and an enlarged, generally annular catch 10 formed at the proximal end. The cutting surface of needle 8 projects outwardly from the cylinder 2, and the needle catch 10 is located at the distal aspect of cylinder 2 to perform an important function which will be described in greater detail hereinafter.

Located within and adapted for reciprocal axial movement through the cylinder 2 is a piston 14. Piston 14 comprises the detachable connection of an elongated stem 16 to a sealing and locking assembly 18. The piston stem 16 is preferably, but not necessarily, hollow to facilitate a quick and relatively easy detachment of the stem 16 from the sealing and locking assembly 18 (in a manner to be described in greater detail when referring to FIG. 3). Formed around a proximal end of the stem 16 is a flange 19. Stem 16 is connected at the distal end thereof to a conical locking skirt 20 which is formed of a resilient material. The skirt 20 may have a plurality of slots 22 formed therealong to create a series of flexible locking fingers. The stem 16 and locking skirt 20 are connected to one another at opposite sides of a narrow groove 24 which is formed around the periphery of stem 16 to provide the stem with an area of reduced cross-section to thereby facilitate the detachment of the stem 16 from the sealing and locking assembly 18.

The sealing and locking assembly 18 includes a locking flange 26 which is coextensively connected to and spaced distally from the conical flange 20 by way of a neck portion 28. Coextensively formed with and extending distally from the locking flange 26 are one or more pairs of oppositely disposed, flexible legs 30 between which is formed a hollow receptacle 32 for selectively capturing the catch 10 of the needle 8. That is to say, the needle 8, the catch 10 thereof, and the hollow needle capturing receptacle 32 are concentrically aligned with one another so that the needle catch 10 may be snapped into receipt by the receptacle 32 when piston 14 is moved to the most distal aspect of syringe cylinder 2 (best illustrated in FIG. 2).

Extending into the receptacle 32 from each of the flexible legs 30 is a tapered lip 34. As will be disclosed in greater detail when referring to FIG. 2, the lip portions 34 of legs 30 are snapped into engagement with the needle catch 10 whereby to permanently retain the needle catch within the receptacle 32 and prevent the withdrawal of catch 10 from receptacle 32.

Extending laterally from each of the legs 30 is a seal retaining flange 36. An elastomeric seal 40 is mounted upon the legs 30 and against the locking flange 36. The seal retaining flange 36 engages the seal and prevents the removal thereof during a displacement of the piston 14 through cylinder 2.

The elastomeric seal 40 includes a proximally extending base 42 which lies adjacent and is supported by the locking flange 26. Seal 40 also includes a distally extending sealing head 44 which is shaped so as to form a fluid-tight seal against the closed distal end of the cylinder 2 when the sealing and locking assembly 18 of piston 14 is moved to the most distal aspect of the syringe 1. A centrally disposed pocket 46 is formed through the sealing head 44 of seal 40 to permit the needle catch 10 of the needle 8 to be snapped into engagement with the lips 34 of legs 30 at needle capturing receptacle 32.

Figure 2:
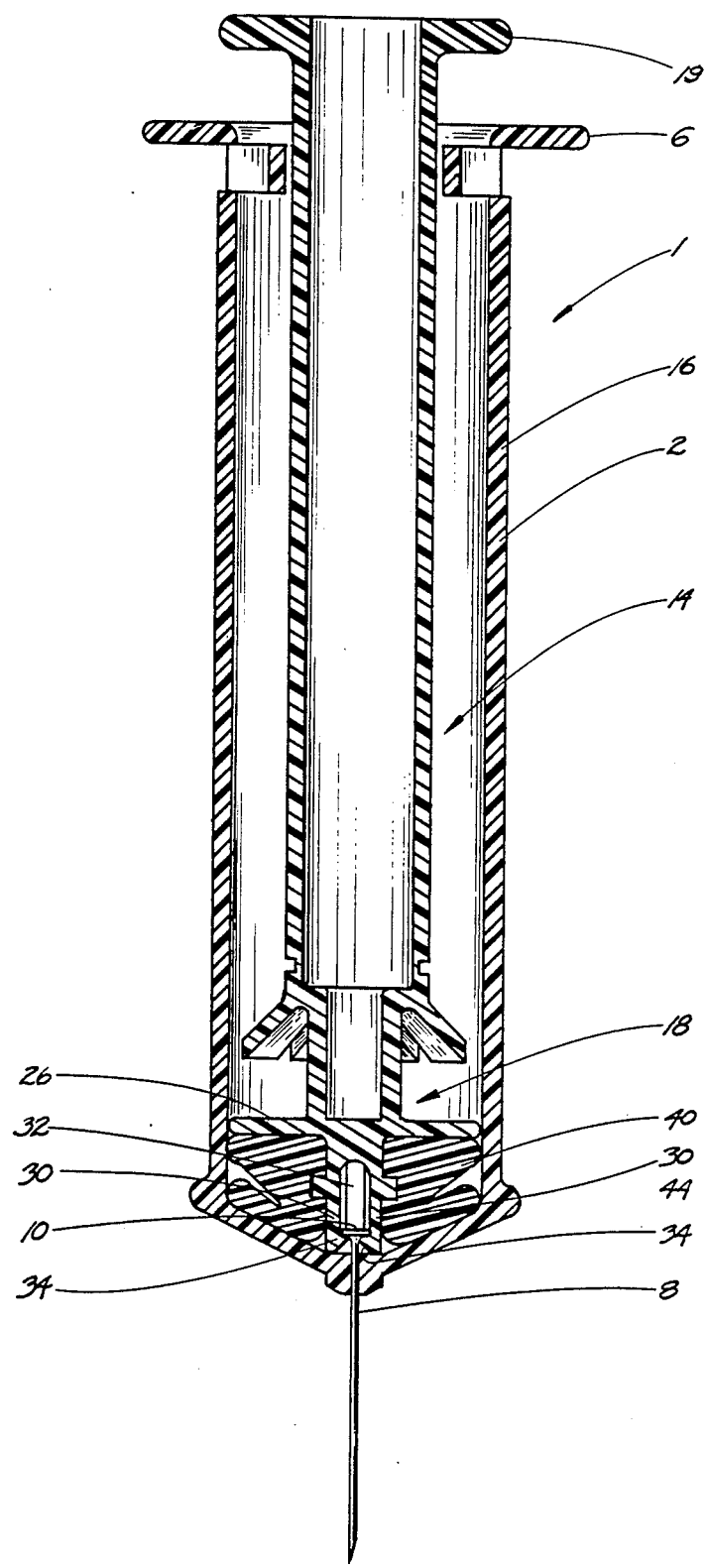
FIG. 2 is a cross-section of the syringe of FIG. 1 showing the piston engaging a needle at the most distal aspect of the syringe cylinder.
Figure 3:
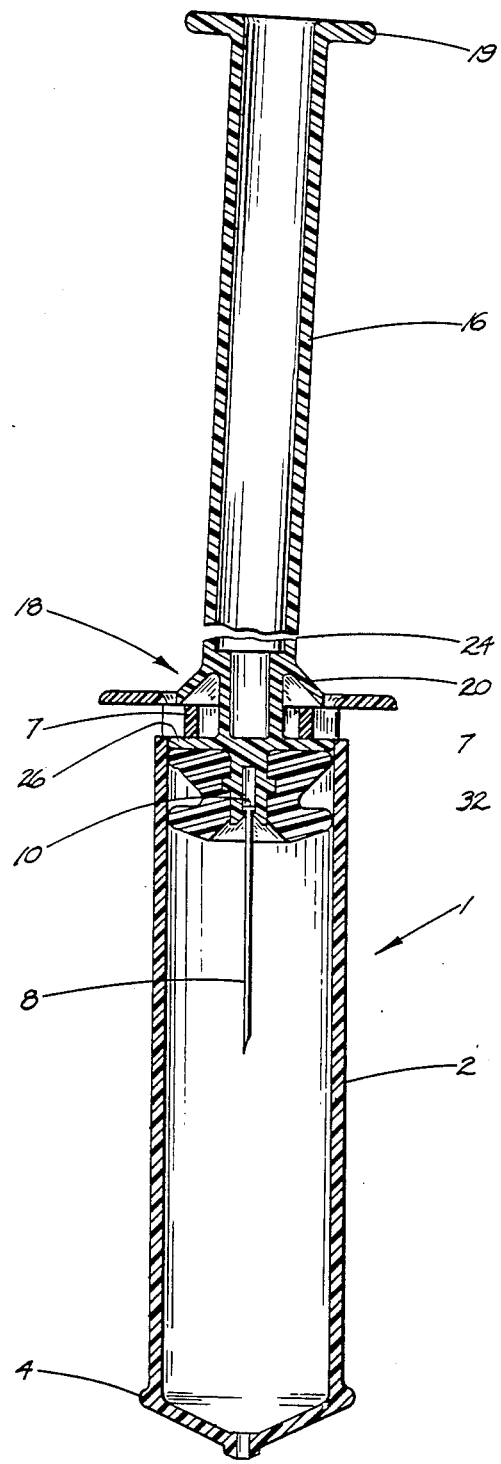
FIG. 3 is a cross-section of the syringe of FIG. 1 showing the needle relocated from the distal end to a proximal end of the syringe cylinder.

The operation of the disease control syringe 1 of the present invention is now described while referring to FIGS. 1-3 of the drawings. Initially, the needle 8 of the syringe 1 of FIG. 1 is moved into fluid communication with a fluid drug supply (not shown). The syringe 1 is infused with fluid medication in a conventional manner by grasping the cylinder 2 behind the anti-slip flange 4 and pulling the stem flange 19 of piston stem 16 to withdraw the piston 14 proximally and axially through the cylinder 2. Once the syringe is infused with medication, a conventional injection procedure may be executed by depressing the stem flange 19 and driving the piston distally through the cylinder 2.

At the conclusion of the injection procedure, and referring now to FIG. 2 of the drawings, the piston 14 is moved completely and axially through the cylinder 2 of syringe 1. The sealing and locking assembly 18 of piston 14 is thereupon moved to the most distal aspect of the syringe 1, whereby the sealing head 44 of elastomeric seal 40 is located flush against the closed distal end of cylinder 2. Next, the syringe 1 is supported at the major flange 6 thereof and the piston 14 is depressed distally while applying an axial force against the flange 19 of piston stem 16. Such axial force is transmitted from the stem 16 to the elastomeric seal 40 by way of the locking flange 46 upon which seal 40 is seated. Because of the resiliency of the seal 40, the sealing head 44 thereof is moved towards and compressed against the closed distal end of syringe cylinder 2. The compression and distal displacement of sealing head 44 correspondingly advances the flexible legs 30 of sealing and locking assembly 18 into engagement with the catch 10 of needle 8.

More particularly, the movement of the tapered lips 34 of the flexible legs 30 into engagement with the needle catch 10 causes a slight clockwise rotation and separation of the legs 30 so as to permit the catch 10 to be snapped into receipt by the needle capturing receptacle 32. After the needle catch 10 is moved past the lips 34 and into receptacle 32, the flexible legs 30 are automatically rotated counterclockwise to establish a positive locking feature for preventing the removal of the needle catch 10 from receptacle 32. That is, the lips 34 of legs 30 form shoulders or stops against which the needle catch 10 is seated when the catch is received within needle capturing receptacle 32. Such shoulders or stops establish a sufficiently narrow exit from cylinder 2 between opposing legs 30 to permanently prevent any removal of the needle catch 10 outwardly from the receptacle 32.

In FIG. 3 of the drawings, the needle 8 (with the catch 10 thereof permanently retained within needle capturing receptacle 32) is retracted from the distal end of cylinder 2 of syringe 1 and relocated at the proximal end thereof. The syringe cylinder 2 is grasped behind the anti-slip flange 4, and the flange 19 of piston stem 16 is withdrawn proximally (in the direction of the reference arrows) and outwardly of the cylinder 2.

More particularly, the stem 16 is moved through the open proximal end of cylinder 2, whereby the conical locking skirt 20 is correspondingly moved into engagement, and then past the internal locking tabs 7. The movement of the resilient locking skirt 20 into engagement with locking tabs 7 causes a compression of the locking skirt 20 to permit the skirt to be moved past the locking tabs. Once the resilient locking skirt 20 is moved past locking tabs 7 and through the open proximal end of cylinder 2, the previously compressed locking skirt 20 is relaxed and automatically returned to its pre-compressed shape to prevent the return of the locking skirt to the interior cylinder 2 via the open proximal end thereof. This is to say, the relatively large diameter base of conical skirt 20 is seated upon the locking tabs 7. As previously disclosed when referring to FIG. 1, the locking tabs 7 establish a relatively narrow diameter opening at the proximal end of cylinder 2 to form a stop, whereby to block the return of locking skirt 20 and, therefore, the piston stem 16 to the interior of cylinder 2.

What is more, relocating the needle 8 to the proximal end of cylinder 2 correspondingly moves the locking flange 26 axially through the cylinder 2 and into engagement with locking tabs 7 across the proximal end of the cylinder. However, the locking tabs 7 act as a stop to prevent the removal of the locking flange 26 (as well as the needle capturing chamber 32 at which needle 8 is permanently retained from the proximal end of cylinder 2. Therefore, the needle 8 projects from the proximal end and is located completely within the walls of the cylinder 2 of syringe 1.

When the piston stem 16 is completely withdrawn from the syringe cylinder 2 and the needle 8 is relocated from the distal to the proximal cylinder end, the stem 16 may be detached from the sealing and locking assembly 18. With the locking skirt 20 and the locking flange 26 of the sealing and locking assembly 18 immovably disposed at opposite sides of the locking tabs 7 and across the proximal end of cylinder 2, a sufficient bending force is exerted upon the piston stem 16 to fracture the stem along the groove 24 formed around the periphery thereof. The piston stem 16 is then discarded. However, the locking skirt 20 and the locking flange 26 remain anchored at opposite sides of the locking tabs 7 to seal off the proximal end of cylinder 2 and thereby block across to the needle 8 at the interior of the cylinder. More particularly, the needle cannot be removed from the cylinder 2, because locking tabs 7 prevent both the movement of locking flange 26 therepast and the withdrawal of needle 8 from cylinder 2. Moreover, the syringe cylinder cannot be reused, because locking tabs 7 also prevent both the movement of conical locking skirt 20 therepast, and the return of the needle 8 to the distal end of cylinder 2. Accordingly, the needle capturing receptacle 32 is locked at its final position in cylinder 2 (with the needle catch 10 permanently retained in receptacle 32), so as to create a self-contained disposal cartridge with the needle cannula shielded and rendered irretrievable therewithin.

By virtue of the present invention, a needle can be retracted and sealed within the syringe cylinder, whereby to render an emptied syringe safe from accidental needle strikes by eliminating the need for health care workers to either handle or cut the needle as has heretofor been required with conventional syringes. In addition, reuse of the emptied syringe for possible drug related purposes is prevented, inasmuch as the needle is permanently and irretrievable locked within the syringe cylinder. Thus, the spread of contagious disease as has been caused, in the past, by either an accidental needle strike or the reuse of a contaminated syringe by a drug abuser may be avoided.

It will be apparent that while a preferred embodiment of the invention has been shown and described, various modifications and changes may be made without departing from the true spirit and scope of the invention.

Having thus set forth a preferred embodiment of the invention, what is claimed is:

1. A disease control syringe comprising:
    a hollow syringe cylinder having a closed distal end and an open proximal end;
    a needle being detachably connected to said cylinder and having a first end projecting through the distal end of said cylinder and a second end located within said cylinder;
    a piston assembly movable reciprocally through said cylinder and having a needle capturing receptacle to selectively receive and engage the second end of said needle at said distal cylinder end for detaching said needle from said distal end for relocation towards said proximal cylinder end, such that said needle extends completely within the interior of said cylinder from said proximal end, said needle capturing receptacle being formed between a plurality of flexible legs which are adapted to bend to permit the receipt of the second end of said needle within said receptacle;
    a locking tab extending inwardly from said syringe cylinder;
    a locking flange extending outwardly from said piston assembly and movable therewith through said cylinder; and
    a flexible locking skirt extending outwardly from said piston assembly and being spaced axially and proximally from said locking flange, said locking skirt being movable with said piston assembly to be moved into contact with and then past said locking tab when said needle is relocated by said piston assembly towards the proximal end of said cylinder, such that said locking tab is located in the space between said locking skirt and said locking flange;
    said locking flange, said locking tab, and said locking skirt cooperating with one another when said locking tab is located between said skirt and said flange to block the movement of said piston assembly through said cylinder and thereby prevent the removal of said needle outwardly through the proximal end of said cylinder and a return of said needle from said proximal end to the distal end of said cylinder.

2. The syringe recited in claim 1, wherein the second end of said needle has a needle catch formed thereat, said needle catch being received within said needle capturing receptacle to connect said piston assembly to said needle.

3. The syringe recited in claim 1, wherein said piston assembly includes a resilient sealing head extending around said needle capturing receptacle, said sealing head expulsing fluid through said needle when said piston assembly is moved distally through said syringe cylinder during an injection procedure, and said sealing head being compressed against the distal aspect of said cylinder for axially advancing said needle capturing receptacle into engagement with the second end of said needle.

4. The syringe recited in claim 1, wherein each of said flexible legs includes a tapered lip extending inwardly of said needle capturing receptacle to prevent the withdrawal of said second needle end from said receptacle after said needle has been received therewithin.

5. The syringe recited in claim 1, wherein said piston assembly comprises an elongated stem connected to said needle engaging means, said stem being detachable from said needle engaging means after said needle has been relocated from the distal end to the proximal end of said cylinder.

6. A syringe comprising a hollow cylinder having a substantially closed distal end and an open proximal end and a needle having a first end extending from said distal end and a second end communicating with the interior of said cylinder, said syringe further comprising:

piston assembly means movable axially and reciprocally through said cylinder and having a needle capturing receptacle for selectively engaging the second end of said needle at the distal end of said cylinder and for relocating said needle from the distal end of said cylinder to a relatively proximal position within said cylinder, the second end of said needle having a relatively large needle catch which is to be irremovably received within said needle capturing receptacle to permanently connect said needle to said piston assembly means, said needle capturing receptacle being formed between a plurality of flexible legs, each of said legs terminating at an inwardly projecting lip, said needle catch being received within said receptacle and below the respective lips of said legs to prevent the withdrawal of said needle catch from said receptacle after said needle catch has been received therewithin; and means cooperating with said cylinder by which to permanently anchor said needle at the relatively proximal portion within said cylinder, said anchoring means preventing the axial displacement of said needle through said cylinder, such that said needle may neither be removed from the proximal end of said cylinder nor returned to the distal end of said cylinder.

7. The syringe recited in claim 6, wherein said piston assembly means has a resilient plunger formed at the first end thereof, said plunger surrounding said needle capturing receptacle and extending slightly forward thereof, said plunger being adapted to expulse fluid through said needle when said piston assembly means is moved distally through said cylinder during an injection procedure, and said plunger being compressed against the distal end of said cylinder for axially advancing said needle capturing receptacle into engagement with the needle catch of said needle.

8. The syringe recited in claim 6, wherein said piston assembly comprises an elongated stem by which to move said piston assembly through said cylinder, said stem being detachable from said piston assembly and removable from said cylinder through the proximal end thereof after said needle has been relocated from the distal end of said cylinder and anchored at said proximal position within said cylinder.

9. A disease control syringe having a retractable needle and comprising:

a hollow syringe cylinder having a substantially closed distal end and an open proximal end;

a needle projecting through the distal end of the cylinder, such that a first end of said needle extends outwardly from said cylinder for administering an injection and a second end of said needle extends inwardly into the interior of said cylinder, said second end having a catch which is spaced axially from the distal end of said cylinder;

a piston assembly movable axially and reciprocally through said cylinder and having a needle capturing receptacle in which to receive and retain the catch at the second end of said needle for retracting said needle through said distal end and relocating said needle towards the proximal end of said cylinder, whereby said needle is located completely within the interior of said cylinder, said needle capturing receptacle being formed between a plurality of flexible legs which engage and retain said catch within said receptacle;

first and second locking flanges spaced axially from one another and projecting from one of said piston assembly or said cylinder; and a locking tab projecting from the other one of said piston assembly or said cylinder, said locking tab being received in the space between said first and second locking flanges when said piston assembly relocates said needle toward the proximal end of said cylinder so as to prevent an additional axial movement of said piston assembly and block the return of said needle to the distal end of said cylinder and the removal of said needle from the proximal end of said cylinder.

10. The syringe recited in claim 9, wherein said needle is detachably connected to and retained by the distal end of said cylinder, said piston assembly detaching said needle from said distal end for relocation towards the proximal end of said cylinder.

11. The syringe recited in claim 9, wherein said first and second locking flanges are flexible and inflexible members, respectively, the movement of said piston assembly causing said locking tab to communicate with and thereby bend said flexible locking flange until said locking tab is located between said locking flanges to prevent the additional axial movement of said piston assembly and block the return and removal of said needle.

12. The syringe recited in claim 9, wherein said piston assembly comprises an elongated stem by which to move said piston assembly through said cylinder, said stem being detachable from said piston assembly and removable from said cylinder through the proximal end thereof after said needle has been retracted through the distal end of said cylinder and relocated toward said proximal end.

* * * * *